United States Patent [19]

Suzuki et al.

[11] Patent Number: 5,756,735
[45] Date of Patent: May 26, 1998

[54] XANTHINE DERIVATIVES

[75] Inventors: Fumio Suzuki, Mishima; Akio Ishii, Sunto-gun; Hiromi Nonaka, Sunto-gun; Nobuo Kosaka, Sunto-gun; Shunji Ichikawa, Tagata-gun; Junichi Shimada, Sunto-gun, all of Japan

[73] Assignee: Kyowa Hakko Kogyo Co., Ltd., Tokyo, Japan

[21] Appl. No.: 483,159

[22] Filed: Jun. 7, 1995

Related U.S. Application Data

[63] Continuation of Ser. No. 39,193, filed as PCT/JP91/01420, published as WO92/06976, abandoned.

[30] Foreign Application Priority Data

Oct. 18, 1990 [JP] Japan ................................ 2-280171

[51] Int. Cl.$^6$ .................................................. C07D 473/06
[52] U.S. Cl. ........................ 544/267; 544/269; 544/270; 544/273
[58] Field of Search ........................ 544/269, 267, 544/270, 273

[56] References Cited

U.S. PATENT DOCUMENTS 3,641,010  2/1972  Schweiss et al. ................... 544/273
5,270,316  12/1993  Suzuki ............................... 544/273

FOREIGN PATENT DOCUMENTS 0423805  4/1991  European Pat. Off. .
930211  7/1955  Germany .

OTHER PUBLICATIONS

Trivedi et al., *Structure–Activity Relationships of Adenosine A1 and A2 Receptors*, Adenosine and Adenosine Receptors, Williams ed. (1990) Ch.3, 57–103.
Erickson et al., J. Med. Chem., vol. 34, No. 4 (1991) 1431:5.
Kaupp et al., Chem. Ber. vol. 119 (1986) 1525:39.
Lugovkin, Chem Abs 60, 1741g (1963).
Kalu, Bone and Mineral 14, 175–187 (1991).
Jacobson, J Med Chem 35, 407 (1992).

*Primary Examiner*—Mark L. Berch
*Attorney, Agent, or Firm*—Fitzpatrick, Cella, Harper & Scinto

[57] ABSTRACT

The present invention relates to novel xanthine derivatives of the formula (I) which are selectively antagonistic to an adenosine $A_2$ receptor, and pharmaceutically acceptable salts thereof. Formula (I):

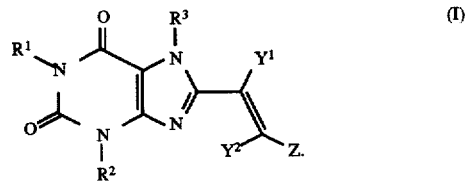

In the formula, $R^1$ and $R^2$ are the same or different and each represents a hydrogen atom, a propyl group, a butyl group or an allyl group; $R^3$ represents a hydrogen atom or a lower alkyl group; $Y^1$ and $Y^2$ are the same or different and each represents a hydrogen atom or a methyl group; and Z represents a substituted or unsubstituted phenyl group, a pyridyl group, an imidazolyl group, a furyl group or a thienyl group.

1 Claim, No Drawings

XANTHINE DERIVATIVES

This application is a continuation of application Ser. No. 08/039,193, filed as PCT/JP91/01420 published as WO92/06976, now abandoned.

TECHNICAL FIELD

The present invention relates to novel 8-substituted xanthine derivatives having adenosine $A_2$ receptor-antagonistic activity (hereinafter referred to as anti-$A_2$ activity). The novel 8-substituted xanthine derivatives having anti-$A_2$ activity exhibit a therapeutic effect on asthma and osteoporosis.

BACKGROUND ART

It is known that adenosine exhibits bronchospasmic activity and bone absorption promoting activity via an $A_2$ receptor. Therefore, adenosine $A_2$ receptor-antagonists (hereinafter referred to as $A_2$-antagonists) are expected as anti-asthmatic agents and therapeutic agents for osteoporosis.

Japanese Published Examined Patent Application No. 26516/72 discloses, as cerebro-stimulating agents, compounds of the following formula (A):

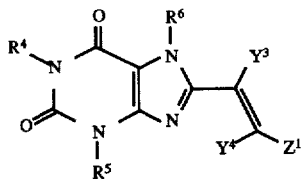

(A)

wherein $R^4$ and $R^5$ are the same or different and each represents methyl or ethyl, $R^6$ represents methyl, $Y^3$ and $Y^4$ each represents hydrogen, and $Z^1$ represents phenyl or 3,4,5-trimethoxyphenyl.

Of the compounds of the formula (A) wherein $R^4$, $R^5$ and $R^6$ are methyl and $Y^3$ and $Y^4$ are hydrogen, a compound wherein $Z^1$ is phenyl (8-styrylcaffeine) (Chem. Ber., Vol. 119, page 1525, 1986) and compounds wherein $Z^1$ is pyridyl, quinolyl, or methoxy-substituted or unsubstituted benzothiazolyl (Chem. Abst., Vol. 60, 1741h, 1964) are known, but there is no description of the pharmacological activity of them.

DISCLOSURE OF THE INVENTION

The present invention relates to xanthine derivatives of the formula (I):

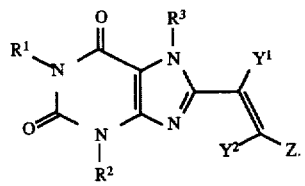

(I)

wherein $R^1$ and $R^2$ are the same or different and each represents a hydrogen atom, a propyl group, a butyl group or an allyl group; $R^3$ represents a hydrogen atom or a lower alkyl group; $Y^1$ and $Y^2$ are the same or different and each represents a hydrogen atom or a methyl group; and Z represents a substituted or unsubstituted phenyl group, a pyridyl group, an imidazolyl group, a furyl group or a thienyl group, and their pharmaceutically acceptable salts.

In the definitions of the groups in the formula (I), the lower alkyl group means a straight-chain or branched alkyl group having 1 to 6 carbon atoms, for example, methyl, ethyl, propyl, isopropyl, butyl, isobutyl, sec-butyl, tert-butyl, pentyl, neopentyl and hexyl. The phenyl group may have one to three substituents, which are the same or different and are, for example, lower alkyl, hydroxy, lower alkoxy, halogen, amino, and nitro. The lower alkyl and the alkyl moiety in the lower alkoxy have the same meaning as the above-mentioned lower alkyl group. The halogen includes fluorine, chlorine, bromine and iodine atoms.

The pharmaceutically acceptable salts of Compounds (I) include, for example, pharmaceutically acceptable acid addition salts, metal salts, ammonium salts, organic amine addition salts and amino acid addition salts of them.

As the pharmaceutically acceptable acid addition salts of Compounds (I), there are inorganic acid addition salts such as hydrochloride, sulfate, and phosphate, and organic acid addition salts such as acetate, maleate, fumarate, tartrate, and citrate. As the pharmaceutically acceptable metal salts, there are alkali metal salts such as sodium salt and potassium salt, alkaline earth metal salts such as magnesium salt and calcium salt, aluminum salt, and zinc salt. As the ammonium salts, there are ammonium salt, tetramethylammonium salt, and the like. As the pharmaceutically acceptable organic amine addition salts, there are morpholine addition salt, piperidine addition salt, and the like. As the pharmaceutically acceptable amino acid addition salts, there are lysine addition salt, glycine addition salt, phenylalanine addition salt, and the like.

The processes for producing Compounds (I) are described below.

Process 1

Compounds (Ia), which are Compounds (I) wherein $R^3$ is a hydrogen atom, can be obtained according to the following reaction steps:

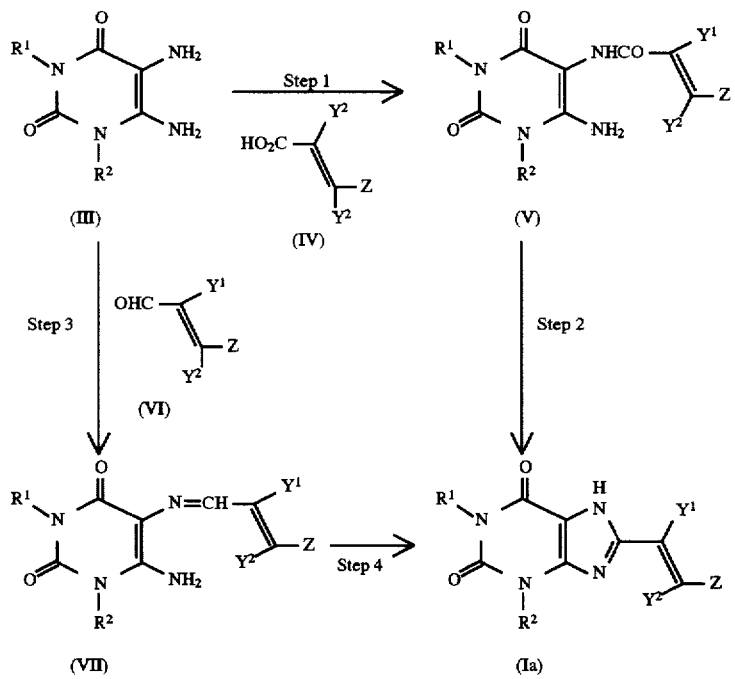

In the formulae, $R^1$, $R^2$, $Y^1$, $Y^2$ and Z have the same meanings as defined above.

Step 1

A uracil derivative (III) is reacted with a carboxylic acid (IV) or its reactive derivative to give Compound (V).

Compound (III) can be obtained by a known method (for example, as described in Japanese Published Unexamined Patent Application No. 42383/84). Examples of the reactive derivative of Compound (IV) are acid halides such as acid chloride and acid bromide, active esters such as p-nitrophenyl ester and N-oxysuccinimide, commercially available acid anhydrides, acid anhydrides formed by using carbodiimide such as 1-ethyl-3-(3-dimethylaminopropyl)-carbodiimide, diisopropylcarbodiimide or dicyclohexylcarbodiimide, and mixed acid anhydrides with monoethyl carbonate or monoisobutyl carbonate.

When Compound (IV) is employed, the reaction is carried out in the absence of a solvent at 50° to 200° C. and is completed in 10 minutes to 5 hours.

When a reactive derivative of Compound (IV) is employed in the step, the reaction can be carried out according to an ordinary process which is generally employed in the field of peptide chemistry. For instance, Compound (III) is reacted with the reactive derivative of Compound (IV), preferably in the presence of an additive or a base, to obtain Compound (V).

A reaction solvent may suitably be selected from halogenated hydrocarbons such as methylene chloride, chloroform and dichloroethane, ethers such as dioxane and tetrahydrofuran, dimethylformamide, dimethylsulfoxide, and water. As the additive, 1-hydroxybenzotriazole and the like may be used, and as the base, pyridine, triethylamine, dimethylaminopyridine, N-methylmorpholine, and the like may be used.

The reaction is carried out at −80° to 50° C. and is completed in 0.5 to 24 hours. The reactive derivative may be formed in the reaction system and directly used without isolation.

Step 2

Compound (Ia) can be obtained by reaction of Compound (V) in the presence of a base (Method A) or a dehydrating agent (Method B) or by heating (Method C).

In Method A, an alkali metal hydroxide such as sodium hydroxide or potassium hydroxide is employed as the base. As a reaction solvent, water, lower alcohols such as methanol and ethanol, ethers such as dioxane and tetrahydrofuran, dimethylformamide, dimethylsulfoxide, and the like may be used alone or in combination. The reaction is carried out at 0° to 180° C. and is completed in 10 minutes to 16 hours.

In Method B, a thionyl halide such as thionyl chloride, or a phosphorus oxyhalide such as phosphorus oxychloride is employed as the dehydrating agent. The reaction may be carried out in a solvent inert to the reaction or in the absence of a solvent. Examples of the inert solvent are halogenated hydrocarbons such as methylene chloride, chloroform and dichloroethane, dimethylformamide, and dimethylsulfoxide. The reaction is carried out at 0° to 180° C. and is completed in 0.5 to 12 hours.

In Method C, a polar solvent such as dimethylsulfoxide, dimethylformamide or Dowtherm A (Dow Chemicals) is employed as a reaction solvent. The reaction is carried out at 50° to 200° C. and is completed in 10 minutes to 5 hours.

Step 3

Compound (III) is reacted with an aldehyde (VI) to give a Schiff base (VII).

As a reaction solvent, mixtures of acetic acid and a lower alcohol such as methanol or ethanol may be used. The reaction is carried out at −20° to 100° C. and is completed in 0.5 to 12 hours.

Step 4

Compound (VII) is subjected to oxidative cyclization in the presence of an oxidizing agent to give Compound (Ia).

Examples of the oxidizing agent are oxygen, ferric chloride, ammonium ceric nitrate, and diethyl azodicarboxylate.

As a reaction solvent, a solvent inert to the reaction is employed. For example, lower alcohols such as methanol and ethanol, halogenated hydrocarbons such as methylene chloride and chloroform, and aromatic hydrocarbons such as toluene, xylene and nitrobenzene may be used. The reaction is carried out at 0° to 180° C. and is completed in 10 minutes to 12 hours.

Process 2

Compounds (Ib), which are Compounds (I) wherein $R^3$ is a lower alkyl group, can be obtained from Compounds (Ia) obtained in Process 1.

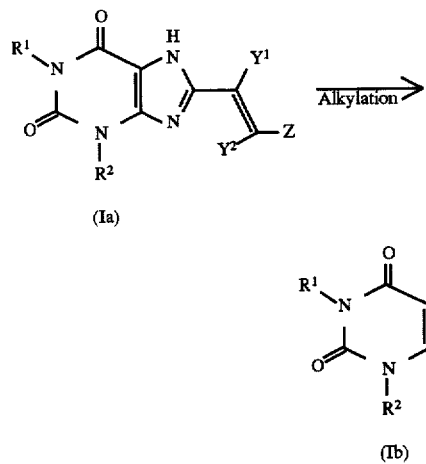

(Ia)

(Ib)

In the formulae, $R^1$, $R^2$, $Y^1$, $Y^2$ and Z have the same meanings as defined above; and $R^{3b}$ represents a lower alkyl group in the definition of $R^3$.

Compound (Ia) is reacted with an alkylating agent, in the presence of a base if necessary, to give Compound (Ib). Examples of the suitable alkylating agent are alkyl halides such as methyl iodide, dialkylsulfates such as dimethylsulfate, and diazoalkanes such as diazomethane.

As the base, alkali metal carbonates such as sodium carbonate and potassium carbonate, alkali metal hydrides such as sodium hydride, alkali metal alkoxides such as sodium methoxide and sodium ethoxide, and the like may be used. The reaction is carried out at 0° to 180° C. and is completed in 0.5 to 24 hours.

Compounds (Ib) wherein Z is an imidazolyl group can also be obtained by alkylating the starting Compounds (Ia) wherein Z is a protected imidazolyl group in the same manner as above and then removing the protecting group.

As the protecting group for the imidazolyl group, a trityl group, a tosyl group, a benzyl group, a benzyloxycarbonyl group, etc. may be mentioned.

The intermediates and the final products produced in the processes described above can be isolated and purified by purification methods which are generally employed in the field of organic synthetic chemistry, for example, filtration, extraction, washing, drying, concentration, recrystallization and various kinds of chromatography. If desired, the intermediates may be subjected to the subsequent reaction without purification.

In the case where a salt of Compound (I) is desired and it is produced in the form of the desired salt, it can be directly subjected to purification. In the case where Compound (I) is produced in the free state and its salt is desired, the salt can be formed by dissolving or suspending Compound (I) in a suitable organic solvent and adding an acid or a base to the solution or suspension.

Compounds (I) and their pharmaceutically acceptable salts may exist as adducts with water or various solvents, which are also within the scope of the present invention.

Some of Compounds (I) can exist in the form of optical isomers. All possible stereoisomers of Compounds (I) and their mixtures, including such optical isomers, are within the scope of the present invention.

Examples of Compounds (I) are shown in Table 1.

TABLE 1

| Compound | −R¹ | −R² | −R³ | −Y¹ | −Y² | −Z |
|---|---|---|---|---|---|---|
| 1 | −(CH₂)₂CH₃ | −(CH₂)₂CH₃ | −H | −H | −H | phenyl |
| 2 | " | " | −CH₃ | " | " | " |
| 3 | " | " | −H | −CH₃ | " | " |
| 4 | " | " | −CH₃ | " | " | " |
| 5 | " | " | −H | −H | " | 4-chlorophenyl |
| 6 | " | " | −CH₃ | " | " | " |

TABLE 1-continued

| Compound | -R¹ | -R² | -R³ | -Y¹ | -Y² | -Z |
|---|---|---|---|---|---|---|
| 7 | " | " | -H | " | " | 3,4-dichlorophenyl |
| 8 | " | " | -CH₃ | " | " | " |
| 9 | " | " | -H | " | " | 4-methoxyphenyl |
| 10 | " | " | -CH₃ | " | " | " |
| 11 | -(CH₂)₂CH₃ | -(CH₂)₂CH₃ | -H | -H | -H | 3,4-dimethoxyphenyl |
| 12 | " | " | -CH₃ | " | " | " |
| 13 | " | " | -H | " | " | 2,3,4-trimethoxyphenyl |
| 14 | " | " | -CH₃ | " | " | " |
| 15 | " | " | -H | " | " | 2-furyl |
| 16 | " | " | -CH₃ | " | " | " |
| 17 | " | " | -H | " | " | 2-thienyl |
| 18 | " | " | -CH₃ | " | " | " |
| 19 | -H | " | -H | " | " | phenyl |
| 20 | -(CH₂)₂CH₃ | " | -H | " | " | 3-pyridyl |
| 21 | " | " | -CH₃ | " | " | 1H-imidazol-4-yl |

TABLE 1-continued

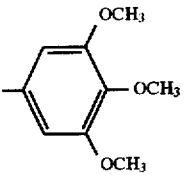

| Compound | −R$^1$ | −R$^2$ | −R$^3$ | −Y$^1$ | −Y$^2$ | −Z |
|---|---|---|---|---|---|---|
| 22 | −H | −(CH$_2$)$_2$CH$_3$ | −H | −H | −H | ![trimethoxyphenyl with OCH$_3$, OCH$_3$, OCH$_3$] |
| 23 | −CH$_2$−CH=CH$_2$ | −CH$_2$−CH=CH$_2$ | " | " | " | " |
| 24 | " | " | −CH$_3$ | " | " | " |
| 25 | −(CH$_2$)$_3$CH$_3$ | −(CH$_2$)$_3$CH$_3$ | −H | " | " | " |
| 26 | " | " | −CH$_3$ | " | " | " |

The pharmacological activity of Compounds (I) is explained below by test examples.

TEST EXAMPLE 1

Adenosine Receptor-Antagonistic Effect:

(1) Adenosine A1 receptor binding test

The test was conducted according to the method of Bruns et al. (Proc. Natl. Acad. Sci., Vol. 77, page 5547, 1980) with slight modification.

The cerebrum of a guinea pig was homogenized in ice-cooled 50 mM tris(hydroxymethyl)aminomethane hydrochloride (hereinafter referred to as Tris-HCl) buffer (pH 7.7) by using a Polytron Homogenizer (manufactured by Kinematicas Co.). The suspension was subjected to centrifugation (50,000×g, 10 minutes), and the precipitate was suspended again in the same amount of 50 mM Tris-HCl buffer. The suspension was centrifuged under the same conditions, and the precipitate obtained was suspended once again in 50 mM Tris-HCl buffer to give a tissue concentration of 100 mg (wet weight)/ml. The resulting tissue suspension was kept at a temperature of 37° C. for 30 minutes in the presence of 0.02 unit/mg tissue of adenosine deaminase (a product of Sigma Co.). The tissue suspension was then subjected to centrifugation (50,000×g, 10 minutes), and 50 mM Tris-HCl buffer was added to the resulting precipitate to form a suspension having a tissue concentration of 10 mg (wet weight)/ml.

To one ml of the thus prepared tissue suspension were added 50 µl of tritium-labeled cyclohexyladenosine ($^3$H-CHA, 27 Ci/mmol; a product of New England Nuclear Co.) (final concentration: 1.1 nM) and 50 µl of a test compound. The resulting mixture was allowed to stand at 25° C. for 90 minutes, and then rapidly filtered by suction through a glass fiber filter (GF/C, a product of Whatman Co.). The filter was immediately washed three times with 5 ml each of ice-cooled 50 mM Tris-HCl buffer and transferred into a vial, and a scintillator (EX-H, a product of Wako Pure Chemical Industries, Ltd.) was added thereto. The radioactivity on the filter was determined with a liquid scintillation counter (Model 4530), manufactured by Packard Instrument Co.).

The inhibition rate of the test compound against the A$_1$ receptor binding ($^3$H-CHA binding) was calculated by the following equation:

$$\text{Inhibition (\%)} = \left(1 - \frac{\text{Amount of binding in the presence of test compound} - \text{Amount of nonspecific binding}}{\text{Amount of total binding} - \text{Amount of nonspecific binding}}\right) \times 100$$

(Notes)

The amount of total binding indicates the radioactivity of $^3$H-CHA bound in the absence of the test compound.

The amount of nonspecific binding indicates the radioactivity of $^3$H-CHA bound in the presence of 10 µM N6-(L-2-phenylisopropyl)adenosine (a product of Sigma Co.).

The amount of binding in the presence of the test compound indicates the radioactivity of $^3$H-CHA bound in the presence of the test compound at indicated concentrations.

The results are shown in Table 2 below. The inhibition constant (Ki value) shown in the table was calculated by the Cheng-Prusoff's equation.

(2) Adenosine A$_2$ receptor binding test

The test was conducted according to the method of Bruns et al. (Mol. Pharmacol., Vol. 29, page 331, 1986) with slight modification.

The final precipitate from the tissue of the rat corpus striatum was obtained by the similar procedure as in the adenosine A$_1$ receptor binding test. In order to adjust the tissue concentration to 5 mg (wet weight)/ml, 50 mM Tris-HCl buffer containing 10 mM magnesium chloride and 0.02 unit/mg tissue of adenosine deaminase (a product of Sigma Co.) was added to the final precipitate.

To one ml of the thus prepared tissue suspension were added 50 µl of a mixture of tritium-labeled N-ethylcarboxyamidoadenosine ($^3$H-NECA, 26 Ci/mmol; a product of Amersham Co.) (final concentration: 3.8 nM) and cyclopentyladenosine (CPA; a product of Sigma Co.) (final concentration: 50 nM), and 50 µl of a test compound. The resulting mixture was allowed to stand at 25° C. for 120 minutes. Then, the amount of radioactivity bound to the A$_2$ receptor was determined in the same manner as in the above A$_1$ receptor binding test.

The inhibition rate of the test compound against the $A_2$ receptor binding ($^3$H-NECA binding) was calculated by the following equation:

$$\text{Inhibition (\%)} = \left(1 - \frac{\text{Amount of binding in the presence of test compound} - \text{Amount of nonspecific binding}}{\text{Amount of total binding} - \text{Amount of nonspecific binding}}\right) \times 100$$

(Notes)

The amount of total binding indicates the radioactivity of $^3$H-NECA bound in the absence of the test compound.

The amount of nonspecific binding indicates the radioactivity of $^3$H-NECA bound in the presence of 100 μM CPA.

The amount of binding in the presence of the test compound indicates the radioactivity of $^3$H-NECA bound in the presence of the test compound at indicated concentrations.

The results are shown in Table 2 below. The Ki value shown in the table was calculated by the following equation.

$$Ki = IC_{50}/(1+L/Kd+C/Kc)$$

(Notes)

In the equation, $IC_{50}$ indicates the concentration at which the inhibition rate is 50%, L indicates the concentration of $^3$H-NECA, Kd indicates the dissociation constant of $^3$H-NECA, C indicates the concentration of CPA, and Kc indicates the inhibition constant of CPA.

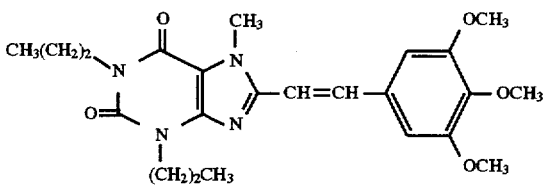

Comparative Compound X

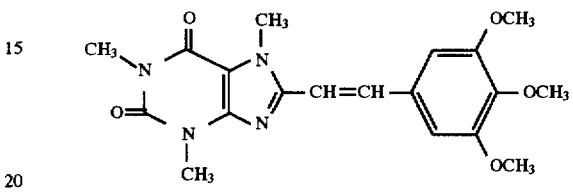

To the culture medium of the calvaria were added 10 μl of the above-mentioned test compound [$10^4$M in the reaction system (control is only DMSO)] and 3 μl of parathyroid hormone (PTH, a product of Sigma) dissolved in 0.15M saline solution [$10^{-8}$M in the reaction system (pH 3)].

Culturing of the bone was carried out under the condition of 95% air and 5% carbon dioxide and at a temperature of 37° C. for 96 hours. The culture medium was renewed 48

TABLE 2

| | $A_1$ Receptor | | | $A_2$ Receptor | | | Ratio of Affinity |
|---|---|---|---|---|---|---|---|
| | Inhibition (%) | | Ki | Inhibition (%) | | Ki | with Receptor |
| Compound | $10^{-5}$ M | $10^{-4}$ M | (nM) | $10^{-5}$ M | $10^{-4}$ M | (nM) | ($A_2/A_1$) |
| 2 | 64 | 82 | 1400 | 95 | 96 | 27 | 52 |
| 10 | 65 | 86 | 2000 | 95 | 95 | 39 | 51 |
| 12 | 61 | 74 | 3100 | 96 | 97 | 13 | 240 |
| 13 | 50 | 57 | 1700 | 91 | 87 | 35 | 49 |
| 14 | 30 | 50 | 65000 | 94 | 92 | 14 | 4600 |
| 24 | 31 | 31 | >100000 | 93 | 96 | 32 | >3100 |

TEST EXAMPLE 2

Inhibitory effect on bone absorption:

The calvaria was excised from a newborn dd mouse (5 to 6 days old) under sterile conditions. The calvaria was washed with a modified Dulbecco phosphate buffer physiological saline solution containing neither calcium nor magnesium (a product of Gibco Oriental), and divided into two parts along the center suture. A modified Dulbecco Eagle medium (1.5 ml) (a product of Gibco Oriental) containing 15% equine serum and 2.5% fetal calf serum which had been inactivated by heating at 56° C. for 20 minutes was added to a half of the calvaria.

Compound 14 and 1,3,7-trimethyl-8-[(E)-3,4,5-trimethoxystyryl]xanthine (hereinafter referred to as Comparative Compound X; Japanese Published Examined Patent Application No. 26516/72) each having the following structure were separately dissolved in dimethylsulfoxide (hereinafter referred to as DMSO). Compound 14:

hours after the start of culturing. For determining the amount of calcium liberated from the bone by the action of PTH (bone absorption), the calcium content in the culture as collected after 96 hours of culturing was measured. The calcium concentration in the culture was measured with Calcium C Test Wako (manufactured by Wako Pure Chemical Industries, Ltd.). The bone absorption rate was calculated using the following equation. The test of significance of the inhibitory effect on bone absorption was performed by the Duncan's multi-weight comparative test.

Inhibition rate (%)

$$=[(C_P-C_D)/(C_P-C_0)]\times 100$$

$C_D$ indicates the total calcium concentration in the culture treated with both the test compound and PTH;

$C_P$ indicates the total calcium concentration in the culture treated with only PTH (control); and $C_0$ indicates the total calcium concentration in the culture containing neither the test compound nor PTH.

The results are shown in Table 3.

TABLE 3

| Test Sample | Ca Concentration (mg/dl) (n = 6, mean +/- S.E.M.) | Inhibition Rate (%) |
|---|---|---|
| Not treated with PTH | 8.44 ± 0.10 | — |
| Control | 12.64 ± 0.14 | — |
| Compound 14 | 7.66 ± 0.08** | 119 |
| Comparative Compound X | 10.32 ± 0.13** | 55 |

**Significant difference between the test compound and the Control ($p < 0.01$)
++Significant difference between Compound 14 and Comparative Compound X (++)

From Table 3 above, it is noted that both Compound 14 and Comparative Compound X significantly inhibited bone absorption by PTH. The bone absorption inhibition rate of Compound 14 was significantly higher than that of Comparative Compound X.

Test Example 3

Mouse locomotor activity:

The mouse locomotor activity after administration of a test compound and theophylline (The Merck Index 11th, 9212, 1989) was observed in the following manner.

Five ddY male mice having a weight of 19 to 21 g were used for one group. A test compound and theophylline were orally administered to the mice and then the mice were put in an acrylic test cage (length 26×width 4533 height 25 cm). The amount of locomotor activity of each mouse was measured with Automex II (manufactured by Columbus) for 3 hours after the administration. Test of significance between the control group and the test compound-administered group was performed by the Student's t-test, and enhancement of the locomotor activity was judged. Furthermore, the minimum effective dose showing a significant difference was determined.

The results are shown in Table 4.

TABLE 4

| Compound | Minimum Effective Dose (mg/kg, p.o.) |
|---|---|
| Compound 2 | 1.25 |
| Compound 12 | 0.63 |
| Compound 14 | 10 |
| Theophylline | 20 |

Table 4 shows that the test compounds having anti-$A_2$ activity enhanced the locomotor activity at a dose less than half of that of theophylline.

Test Example 4

Acute toxicity test:

Three dd male mice having a weight of 20±1 g were used for one group. A test compound was orally administered to the mice.

The mortality was observed 7 days after the administration to determine the minimum lethal dose (MLD).

The results are shown in Table 5.

TABLE 5

| Compound | MLD (mg/kg) |
|---|---|
| 1 | >300 |
| 3 | >300 |
| 4 | >300 |
| 5 | >300 |
| 6 | >300 |
| 7 | >300 |
| 8 | >300 |
| 9 | >300 |
| 10 | >300 |
| 11 | >300 |
| 12 | >300 |
| 13 | >300 |
| 14 | >300 |
| 15 | >300 |
| 17 | >300 |
| 18 | >300 |

Compounds (I) exhibit a potent anti-$A_2$ activity. Therefore, pharmaceuticals containing Compound (I) as an active ingredient are effective for the treatment of various diseases caused by hyperergasia of adenosine $A_2$ receptor.

Compounds (I) and their pharmaceutically acceptable salts can be used as they are or in various pharmaceutical forms. Pharmaceutical compositions of the present invention can be prepared by mixing an effective amount of Compound (I) or its pharmaceutically acceptable salt, as an active ingredient, with a pharmaceutically acceptable carrier. The compositions are preferably in a unit dose form suitable for oral administration or administration through injection.

For preparing compositions for oral administration, useful pharmaceutically acceptable carriers can be used. For instance, liquid preparations for oral administration such as suspension and syrup can be prepared using water, sugars such as sucrose, sorbitol and fructose, glycols such as polyethylene glycol and propylene glycol, oils such as sesame oil, olive oil and soybean oil, preservatives such as p-hydroxybenzoates, flavors such as strawberry flavor and peppermint, and the like. Powders, pills, capsules and tablets can be prepared using excipients such as lactose, glucose, sucrose and mannitol, disintegrators such as starch and sodium alginate, lubricants such as magnesium stearate and talc, binders such as polyvinyl alcohol, hydroxypropyl cellulose and gelatin, surfactants such as fatty acid esters, plasticizers such as glycerine, and the like. Tablets and capsules are the most useful oral unit dose forms because of the readiness of administration. For preparing tablets and capsules, solid pharmaceutical carriers are employed.

An injectable solution can be prepared using a carrier such as distilled water, a salt solution, a glucose solution or a mixture of a salt solution and a glucose solution.

The effective dose and administration schedule of Compounds (I) and their pharmaceutically acceptable salts vary depending upon the administration route, the age, body weight and condition of a patient, etc. However, it is generally preferred to administer the effective compound in a daily dose of 0.01 to 50 mg/kg in 3 to 4 parts.

In addition, Compounds (I) may also be administered by inhalation in the form of aerosol, fine powder or spray solution. In the case of aerosol administration, the compound of the present invention is dissolved in an appropriate pharmaceutically acceptable solvent, such as ethyl alcohol or a combination of miscible solvents, and the resulting solution is mixed with a pharmaceutically acceptable propellant.

Examples and preparation examples of the present invention are shown below.

Example 1

1,3-Dipropyl-8-(E)-styrylxanthine (Compound 1)

5,6-Diamino-1,3-dipropyluracil (U.S. Pat. No. 2,602,795) (6.0 g, 26.5 mmol) was slowly added to a solution of 3.34 ml (26.5 mmol) of cinnamic aldehyde in a mixture of 360 ml of methanol and 15 ml of acetic acid under ice cooling. The mixture was stirred at room temperature for 30 minutes, and then the solvent was distilled off under reduced pressure to give 6.30 g (yield: 70%) of 6-amino-1,3-dipropyl-5-[3-phenyl-3-(E)-propenylidene]uracil (Compound a) as an amorphous substance.

The physicochemical properties of Compound a are shown below.

Melting point: 159.5° to 161.0° C.

IR (KBr), $v_{max}(cm^{-1})$: 1687, 1593

NMR (CDCl$_3$, 90 MHz), δ (ppm): 9.75–9.60(1H, m), 7.60–7.25(5H, m), 7.00–6.80(2H, m), 5.70(brs, 2H), 4.00–3.70(4H, m), 2.00–1.40(4H, m), 1.10–0.75(6H, m)

MS m/e (relative intensity): 340 (100, M$^+$), 130 (86)

Ethanol (240 ml) was added to 6.30 g (18.5 mmol) of Compound a and the mixture was heated under reflux for 2 hours in the presence of 4.32 g (26.5 mmol) of ferric chloride. After cooling, deposited crystals were collected by filtration to give 3.61 g (yield: 61%) of Compound 1 as white crystals.

Melting point: 259.3° to 261.0° C. (recrystallized from ethanol)

Elemental analysis: $C_{19}H_{22}N_4O_2$ Calcd.(%): C, 67.43; H, 6.55; N, 16.56 Found (%): C, 67.40; H, 6.61; N, 16.71

IR (KBr), $v_{max}(cm^{-1})$: 1700, 1650, 1505

NMR (DMSO-d$_6$), δ (ppm): 1.3.59(1H, brs), 7.70–7.55 (3H, m), 7.50–7.30(3H, m), 7.06(1H, d, J=16.5 Hz), 3.99 (2H, t), 3.86(2H, t), 2.80–2.50(4H, m), 0.95–0.80(6H, m)

Example 2

1,3-Dipropyl-7-methyl-8-(E)-styrylxanthine (Compound 2)

Compound 1 obtained in Example 1 (2.00 g, 5.90 mmol) was dissolved in 65 ml of N,N-dimethylformamide. To the solution were added 2.04 g (14.8 mmol) of potassium carbonate and then 0.74 ml (11.8 mmol) of methyl iodide, and the mixture was stirred at 50° C. for 30 minutes. After cooling, insoluble substances were removed by filtration, and 500 ml of water was added to the filtrate. The mixture was extracted three times with chloroform, and the combined organic layers were washed twice with water and twice with a saturated aqueous solution of sodium chloride, and dried over anhydrous sodium sulfate. The solvent was distilled off under reduced pressure. The residue was purified by silica gel column chromatography (eluent: 20% ethyl acetate/hexane), followed by recrystallization from ethanol/water to give 1.75 g (yield: 84%) of Compound 2 as white needles.

Melting point: 162.8° to 163.2° C.

Elemental analysis: $C_{20}H_{24}N_4O_2$ Calcd.(%): C, 68.16; H, 6.86; N, 15.90 Found (%): C, 67.94; H, 6.96; N, 16.15

IR (KBr), $v_{max}(cm^{-1})$: 1690, 1654, 1542, 1450, 1437

NMR (CDCl$_3$), δ (ppm): 7.79(1H, d, J=15.8 Hz), 7.65–7.55(2H, m), 7.48–7.35(3H, m), 6.92(1H, d, J=15.8 Hz), 4.11(2H, t), 4.06(3H, s), 3.98(2H, t), 2.00–1.60(4H, m), 1.08–0.95(6H, m)

Example 3

1,3-Dipropyl-8-[(E)-α-methylstyryl]xanthine (Compound 3)

Substantially the same procedure as in Example 1 was repeated using 5.00 g (22.1 mmol) of 5,6-diamino-1,3-dipropyluracil and 3.08 ml (22.1 mmol) of α-methylcinnamic aldehyde to give 6.73 g (yield: 86%) of 6-amino-1,3-dipropyl-5-(2-methyl-3-phenyl-3-(E)-propenylidene)uracil (Compound b) as an amorphous substance.

NMR (CDCl$_3$, 90 MHz), δ (ppm): 9.58(1H, s), 7.50–7.15 (5H, h), 6.93(1H, brs), 5.64(2H, brs), 4.08–3.80(4H, m), 2.09(3H, s), 2.00–1.50(4H, m), 1.20–0.85(6H, m)

Compound b was treated in substantially the same manner as in Example 1 to give Compound 3 as white crystals.

Melting point: 194.5° to 196.2° C. (recrystallized from ethanol-water)

Elemental analysis: $C_{20}H_{24}N_4O_2$ Calcd.(%): C, 68.16; H, 6.86; N, 15.89 Found (%): C, 67.97; H, 6.64; N, 15.88

IR (KBr), $v_{max}(cm^{-1})$: 1694, 1657, 1651

NMR (CDCl$_3$, 90 MHz), δ (ppm): 12.30(1H, brs), 7.76 (1H, d, J=1.1 Hz), 7.50–7.15(5H, m), 4.15(2H, t), 3.93(2H, t), 2.44(3H, d, J=1.1 Hz), 2.05–1.40(4H, m), 0.99(3H, t), 0.79(3H, t)

Example 4

1,3-Dipropyl-7-methyl-8-[(E)-α-methylstyryl] xanthine(Compound 4)

Substantially the same procedure as in Example 2 was repeated using 2.28 g (6.79 mmol) of Compound 3 obtained in Example 3 to give 1.37 g (yield: 57%) of Compound 4 as white crystals.

Melting point: 106.8° to 109.2° C. (recrystallized from ethanol-water)

Elemental analysis: $C_{21}H_{26}N_4O_2$ Calcd.(%): C, 68.82; H, 7.15; N, 15.28 Found (%): C, 68.82; H, 7.09; N, 15.20

IR (KBr), $v_{max}(cm^{-1})$: 1696, 1657, 1651

NMR (CDCl$_3$, 90 MHz), δ (ppm): 7.50–7.20(5H, m), 6.83(1H, d, J=1.3 Hz), 4.20–3.80(4H, m), 4.05(3H, s), 2.35(3H, d, J=1.3 Hz), 2.00–1.50(4H, m), 1.15–0.85(6H, m)

Example 5

8-[(E)-4-Chlorostyryl]-1,3-dipropylxanthine (Compound 5)

4-Chlorocinnamic acid (4.40 g, 24.3 mmol) and 6.36 g (33.2 mmol) of 1-ethyl-3-(3-diethylaminopropyl) carbodiimide hydrochloride were added to a mixture of dioxane (150 ml) and water (75 ml) containing 5.00 g (22.1 mmol) of 5,6-diamino-1,3-dipropyluracil. The resulting solution was stirred at room temperature for one hour at a pH maintained at 5.5. After the completion of reaction, the solution was adjusted to pH 7 and then extracted three times with chloroform. The extracts were combined, washed with a saturated aqueous solution of sodium chloride, and dried over anhydrous sodium sulfate. The solvent was distilled off under reduced pressure. The residue was purified by silica gel column chromatography (eluent: 3% methanol/chloroform) to give 7.84 g (yield: 91%) of 6-amino-5-[(E)-4-chlorocinnamoyl]amino-1,3-dipropyluracil (Compound c) as an amorphous substance.

NMR (CDCl$_3$, 90 MHz), δ (ppm): 7.78(1H, brs), 7.55(1H, d, J=15.5 Hz), 7.43(2H, d, J=9.0 Hz), 7.28(2H, d, J=9.0 Hz), 6.60(1H, d, J=15.5 Hz), 5.68(2H, brs), 4.05–3.70(4H, m), 2.00–1.50(4H, m), 1.15–0.80(6H, m)

To Compound c (7.84 g, 20.1 mmol) were added 100 ml of dioxane and 100 ml of 2N aqueous solution of sodium hydroxide, followed by heating under reflux for 10 minutes.

After cooling, the mixture was neutralized, and deposited crystals were collected by filtration and recrystallized from dioxane-water to give 6.83 g (yield: 91%) of Compound 5 as white crystals.

Melting point: >290° C.

Elemental analysis: $C_{19}H_{21}ClN_4O_2$ Calcd.(%): C, 61.20; H, 5.67; N, 15.02 Found (%): C, 61.27; H, 5.51; N, 14.91

IR (KBr), $v_{max}(cm^{-1})$: 1700, 1658, 1500

NMR (DMSO-$d_6$), δ (ppm): 13.58(1H, brs), 7.65(2H, d, J=8.5 Hz), 7.62(1H, d, J=16.5 Hz), 7.47(2H, d, J=8.5 Hz), 7.05(1H, d, J=16.5 Hz), 3.99(2H, t), 3.85(2H, t), 1.85–1.55 (4H, m), 1.00–0.88(6H, m)

Example 6

8-[(E)-4-Chlorostyryl]-7-methyl-1,3-dipropylxanthine (Compound 6)

Substantially the same procedure as in Example 2 was repeated using 4.17 g (11.2 mmol) of Compound 5 obtained in Example 5 to give 3.60 g (yield: 83%) of Compound 6 as white needles.

Melting point: 175.0° to 187.2° C. (recrystallized from ethanol)

Elemental analysis: $C_{20}H_{23}ClN_4O_2$ Calcd.(%): C, 62.09; H, 5.99; N, 14.48 Found (%): C, 62.06; H, 5.68; N, 14.36

IR (KBr), $v_{max}(cm^{-1})$: 1697, 1662

NMR (DMSO-d6), δ (ppm): 7.81(2H, d, J=8.4 Hz), 7.63(1H, d, J=15.8 Hz), 7.47(2H, d, J=8.4 Hz), 7.36(1H, d, J=15.8 Hz), 4.03(3H, s), 3.99(2H, t), 3.84(2H, t), 1.85–1.50 (4H, m), 1.00–0.85(6H, m)

Example 7

8-[(E)-3,4-Dichlorostyryl]-1,3-dipropylxanthine (Compound 7)

Substantially the same procedure as in Example 5 was repeated using 5.0 g (22.1 mmol) of 5,6-diamino-1,3-dipropyluracil and 5.27 g (24.3 mmol) of 3,4-dichlorocinnamic acid to obtain 9.43 g (yield: 100%) of 6-amino-5-[(E)-3,4-dichlorocinnamoyl]amino-1,3-dipropyluracil (Compound d) as an amorphous substance.

NMR (CDCl$_3$, 90 MHz), δ (ppm): 8.23(1H, brs), 7.60–7.20(4H, m), 6.63(1H, d, J=15.6 Hz), 5.63(2H, brs), 4.00–3.70(4H, m), 1.95–1.40(4H, m), 1.10–0.80(6H, m)

Substantially the same procedure as in Example 5 was repeated using 9.24 g (21.7 mmol) of Compound d to give 6.03 g (yield: 68%) of Compound 7 as white crystals.

Melting point: 195.3° to 201.6° C. (recrystallized from dimethylsulfoxide-water)

Elemental analysis: $C_{19}H_{20}Cl_2N_4O_2$ Calcd.(%): C, 56.02; H, 4.94; N, 13.75 Found (%): C, 55.88; H, 4.83; N, 13.54

IR (KBr), $v_{max}(cm^{-1})$: 1702, 1644

NMR DMSO-$d_6$), δ (ppm): 13.64(1H, brs), 7.92(1H, d, J=1.5 Hz), 7.70–7.55(3H, m), 7.14(1H, d, J=16.1 Hz), 3.99(2H, t), 3.86(2H, t), 1.80–1.55(4H, m), 1.00–0.85(6H, m)

Example 8

8-[(E)-3,4-Dichlorostyryl]-1,3-dipropyl-7-methylxanthine (Compound 8)

Substantially the same procedure as in Example 2 was repeated using 3.20 g (7.86 mmol) of Compound 7 obtained in Example 7 to give 2.74 g (yield: 83%) of Compound 8 as pale yellow crystals.

Melting point: 125.1° to 135.8° C. (recrystallized from ethanol-water)

Elemental analysis: $C_{20}H_{22}Cl_2N_4O_2$ Calcd.(%): C, 57.01; H, 5.26; N, 13.29 Found (%): C, 57.04; H, 5.02; N, 13.21

IR (KBr), $v_{max}(cm^{-1})$: 1698, 1651

NMR DMSO-$d_6$), δ (ppm): 8.16(1H, s), 7.77(1H, d, J=8.0 Hz), 7.66(1H, d, J=8.0 Hz), 7.61(1H, d, J=15.6 Hz), 7.47 (1H, d, J=15.6 Hz), 4.04(3H, s), 3.99(2H, t), 3.84(2H, t), 1.80–1.50(4H, m), 0.95–0.80(6H, m)

Example 9

1,3-Dipropyl-8-[(E)-4-methoxystyryl]xanthine (Compound 9)

Substantially the same procedure as in Example 5 was repeated using 2.00 g (8.85 mmol) of 5,6-diamino-1,3-dipropyluracil and 1.73 g (9.74 mmol) of 4-methoxycinnamic acid to give 3.17 g (yield: 93%) of 6-amino-1,3-dipropyl-5-[(E)-4-methoxycinnamoyl] aminouracil (Compound e) as an amorphous substance.

NMR (CDCl$_3$, 90 MHz), δ (ppm): 7.78(1H, brs), 7.52(1H, d, J=15.6 Hz), 7.36(2H, d, J=7.8 Hz), 6.79(2H, d, J=7.8 Hz), 6.52(1H, d, J=15.6 Hz), 4.00–3.60(4H, m), 3.79(3H, s), 1.90–1.40(4H, m), 1.10–0.75(6H, m)

Substantially the same procedure as in Example 5 was repeated using 3.11 g (8.06 mmol) of Compound e to give 2.24 g (yield: 76%) of Compound 9 as white needles.

Melting point: 281.1° to 283.8° C. (recrystallized from 2-propanol)

Elemental analysis: $C_{20}H_{24}N_4O_3$ Calcd.(%): C, 65.20; H, 6.56; N, 15.20 Found (%): C, 65.12; H, 6.79; N, 15.48

IR (KBr), $v_{max}(cm^{-1})$: 1694, 1650, 1515

NMR (CDCl$_3$), δ (ppm): 13.03(1H, brs), 7.74(1H, d, J=16.2 Hz), 7.52(2H, d, J=8.9 Hz), 6.97(1H, d, J=16.2 Hz), 6.92(2H, d, J=8.9 Hz), 4.25–4.10(4H, m), 3.86(3H, s), 2.00–1.70(4H, m), 1.05–0.95(6H, m)

Example 10

1,3-Dipropyl-8-[(E)-4-methoxystyryl]-7-methylxanthine (Compound 10)

Substantially the same procedure as in Example 2 was repeated using 1.20 g (3.26 mmol) of Compound 9 obtained in Example 9 to give 1.19 g (yield: 96%) of Compound 10.

Melting point: 159.8° to 161.3° C. (recrystallized from ethanol-water)

Elemental analysis: $C_{21}H_{26}N_4O_3$ Calcd.(%): C, 65.94; H, 6.85; N, 14.64 Found (%): C, 65.92; H, 6.90; N, 14.88

IR (KBr), $v_{max}(cm^{-1})$: 1695, 1658

NMR DMSO-$d_6$), δ (ppm): 7.72(2H, d, J=8.8 Hz), 7.61 (1H, d, J=15.8 Hz), 7.16(1H, d, J=15.8 Hz), 4.05–3.95(2H, m), 4.00(3H, s), 3.83(2H, t), 3.80(3H, s), 1.85–1.50(4H, m), 1.00–0.85(6H, m)

Example 11

8-[(E)-3,4-Dimethoxystyryl]-1,3-dipropylxanthine (Compound 11)

Substantially the same procedure as in Example 5 was repeated using 2.00 g (8.85 mmol) of 5,6-diamino-1,3-dipropyluracil and 2.03 g (9.73 mmol) of 3,4- dimethoxycinnamic acid to give 3.47 g (yield: 94%) of 6-amino-5-[(E)-3,4-dimethoxycinnamoyl]amino-1,3-dipropyluracil (Compound f) as an amorphous substance.

NMR (CDCl$_3$, 90 MHz), δ (ppm): 7.84(1H, brs), 7.50(1H, d, J=15.9 Hz), 7.10–6.65(3H, m), 6.53(1H, d, J=15.9 Hz), 5.75(2H, brs), 4.00–3.50 (4H, m), 3.85(6H, brs), 2.00–1.40 (4H, m), 1.10–0.80(6H, m)

Substantially the same procedure as in Example 5 was repeated using 3.38 g (8.13 mmol) of Compound f to give 2.49 g (yield: 77%) of Compound 11 as white crystals.

Melting point: 260.0° to 263.8° C. (recrystallized from dimethylsulfoxide-water)

Elemental analysis: C$_{21}$H$_{26}$N$_4$O$_4$ Calcd.(%): C, 63.30; H, 6.57; N, 14.06 Found (%): C, 63.29; H, 6.79; N, 14.21

IR (KBr), ν$_{max}$(cm$^{-1}$): 1701, 1640

NMR DMSO-d$_6$), δ (ppm): 13.39(1H, brs), 7.59(1H, d, J=16.7 Hz), 7.26(1H, d, J=1.8 Hz), 7.13(1H, dd, J=1.8, 8.6 Hz), 6.98(1H, d, J=8.6 Hz), 6.95(1H, d, J=16.7 Hz), 3.99 (2H, t), 4.00–3.85(2H, t), 3.83(3H, s), 3.80(3H, s), 1.80–1.55 (4H, m), 1.00–0.85(6H, m)

Example 12

8-[(E)-3,4-Dimethoxystyryl]-1,3-dipropyl-7-methylxanthine (Compound 12)

Substantially the same procedure as in Example 2 was repeated using 1.20 g (3.02 mmol) of Compound 11 obtained in Example 11 to give 1.22 g (yield: 98%) of Compound 12 as white needles.

Melting point: 164.8° to 166.2° C. (recrystallized from 2-propanol-water)

Elemental analysis: C$_{22}$H$_{28}$N$_4$O$_4$ Calcd.(%): C, 64.06; H, 6.84; N, 13.58 Found (%): C, 64.06; H, 6.82; N, 13.80

IR (KBr), ν$_{max}$(cm$^{-1}$): 1692, 1657

NMR DMSO-d$_6$), δ (ppm): 7.60(1H, d, J=15.8 Hz), 7.40(1H, d, J=2.0 Hz), 7.28(1H, dd, J=2.0, 8.4 Hz), 7.18(1H, d, J=15.8 Hz), 6.99(1H, d, J=8.4 Hz), 4.02(3H, s), 3.99(2H, t), 3.90–3.80(2H, m), 3.85(3H, s), 3.80(3H, s), 1.85–1.50 (4H, m), 1.00–0.85(6H, m)

Example 13

1,3-Dipropyl-8-[(E)-3,4,5-trimethoxystyryl]xanthine (Compound 13)

Substantially the same procedure as in Example 5 was repeated using 5.0 g (22.1 mmol) of 5,6-diamino-1,3-dipropyluracil and 5.78 g (24.3 mmol) of 3,4,5-trimethoxycinnamic acid to give 8.06 g (yield: 82%) of 6-amino-1,3-dipropyl-5-[(E)-3,4,5-trimethoxycinnamoyl]aminouracil (Compound h) as an amorphous substance.

NMR (CDCl$_3$, 90 MHz), δ (ppm): 7.85(1H, brs), 7.48(1H, d, J=15.6 Hz), 6.67(2H, s), 6.56(1H, d, J=15.6 Hz), 5.80(2H, brs), 4.00–3.70(4H, m), 3.89(9H, s), 1.80–1.45(4H, m), 1.15–0.80(6H, m)

Substantially the same procedure as in Example 5 was repeated using 10.02 g (22.5 mmol) of Compound h to give 7.90 g (yield: 82%) of Compound 13 as white needles.

Melting point: 161.8° to 162.6° C. (recrystallized from dioxane-water)

Elemental analysis: C$_{22}$H$_{28}$N$_4$O$_5$ Calcd.(%): C, 61.66; H, 6.58; N, 13.07 Found (%): C, 61.73; H, 6.37; N, 13.08

IR (KBr), ν$_{max}$(cm$^{-1}$): 1702, 1643

NMR (CDCl$_3$, 90 MHz), δ (ppm): 12.87(1H, brs), 7.72 (1H, d, J=16.3 Hz), 6.96(1H, d, J=16.3 Hz), 6.81(2H, s), 4.30–3.95(4H, m), 3.92(6H, s), 3.90(3H, s), 2.10–1.50(4H, m), 1.02(2H1, t), 0.90(2H, t)

Example 14

1,3-Dipropyl-7-methyl-8-[(E)-3,4,5-trimethoxystyryl]-xanthine (Compound 14)

Substantially the same procedure as in Example 2 was repeated using 3.50 g (8.18 mmol) of Compound 13 obtained in Example 13 to give 3.44 g (yield: 95%) of Compound 14 as white crystals.

Melting point: 168.4° to 169.1° C. (recrystallized from ethanol-water)

Elemental analysis: C$_{23}$H$_{30}$N$_4$O$_5$ Calcd.(%): C, 62.42; H, 6.83; N, 12.66 Found (%): C, 62.48; H, 6.60; N, 12.70

IR (KBr), ν$_{max}$(cm$^{-1}$): 1698, 1659

NMR (CDCl$_3$, 90 MHz), δ (ppm): 7.71(1H, d, J=15.8 Hz), 6.86(2H, s), 6.78(1H, d, J=15.8 Hz), 4.30–3.95(4H, m), 4.07(3H, s), 3.93(6H, s), 3.90(3H, s), 2.05–1.50(4H, m), 1.20–0.85(6H, m)

Example 15

1,3-Dipropyl-8-[2-(E)-(2-furyl)vinyl]xanthine (Compound 15)

Substantially the same procedure as in Example 5 was repeated using 5.00 g (22.1 mmol) of 5,6-diamino-1,3-dipropyluracil and 3.35 g (24.3 mmol) of 3-(2-furyl)acrylic acid to give 8.02 g of a crude product of 6-amino-1,3-dipropyl-5-[3-(E)-(2-furyl)acryloyl]aminouracil (Compound i) as an amorphous substance.

NMR DMSO-d$_6$-D$_2$O, 90 MHz), δ (ppm): 7.77(1H, d, J=1.5 Hz), 7.21(1H, d, J=15.9 Hz), 6.73(1H, d, J=4 Hz), 6.55(1H, d, J=15.9 Hz), 6.53(1H, dd, J=1.5, 4 Hz), 3.90–3.50(4H, m), 1.70–1.35(4H, m), 1.00–0.60(6H, m)

Substantially the same procedure as in Example 5 was repeated using 8.02 g (22.1 mmol) of Compound i to give 4.81 g (overall yield: 66%) of Compound 15 as a white powder.

Melting point: 258.5° to 259.0° C. (recrystallized from ethanol)

Elemental analysis: C$_{17}$H$_{20}$N$_4$O$_3$ Calcd.(%): C, 62.18; H, 6.13; N, 17.06 Found (%): C, 62.36; H, 6.14; N, 17.29

IR (KBr), ν$_{max}$(cm$^{-1}$): 1698, 1648

NMR DMSO-d$_6$), δ (ppm): 13.48 (1H, brs), 7.78(1H, d, J=1.7 Hz), 7.45(1H, d, J=16.2 Hz), 6.80(1H, d, J=3.4 Hz), 6.75(1H, d, J=16.2 Hz), 6.61(1H, dd, J=1.7, 3.4 Hz), 3.98 (2H, t), 3.85(2H, t), 1.79–1.51(4H, m), 0.95–0.82(6H, m)

Example 16

1,3-Dipropyl-8-[2-(E)-(2-furyl)vinyl]-7-methylxanthine (Compound 16)

Substantially the same procedure as in Example 2 was repeated using 3.02 g (9.21 mmol) of Compound 15 obtained in Example 15 to give 2.60 g (yield: 82%) of Compound 16 as white needles.

Melting point: 161.0° to 161.7° C. (recrystallized from ethanol-water)

Elemental analysis: C$_{18}$H$_{22}$N$_4$O$_3$ Calcd.(%): C, 63.14; H, 6.47; N, 16.36 Found (%): C, 63.37; H, 6.53; N, 16.35

IR (KBr), ν$_{max}$(cm$^{-1}$): 1699, 1651, 1562, 1459

NMR (CDCl$_3$), δ (ppm): 7.54(1H, d, J=5.5 Hz), 7.48(1H, d, J=1.7 Hz), 6.70(1H, d, J=15.5 Hz), 6.57(1H, d, J=3.4 Hz), 6.49(1H, dd, J=1.7, 3.4 Hz), 4.10(2H, t), 4.00(3H, s), 3.95 (2H, t), 1.80–1.65(4H, m), 1.05–0.95(6H, m)

Example 17

1,3-Dipropyl-8-[2-(E)-(2-thienyl)vinyl]xanthine (Compound 17)

Substantially the same procedure as in Example 5 was repeated using 5.0 g (22.1 mmol) of 5,6-diamino-1,3-dipropyluracil and 3.75 g (24.3 mmol) of 3-(2-thienyl) acrylic acid to give 7.33 g (yield: 92%) of 6-amino-1,3-dipropyl-5-[3-(E)-(2-thienyl)acryloyl]-aminouracil (Compound j) as an amorphous substance.

NMR (CDCl$_3$, 90 MHz), δ (ppm): 7.76(1H, brs), 7.72(1H, d, J=15.4 Hz), 7.32 (1H, d, J=5.1 Hz), 7.19(1H, d, J=3.8 Hz), 7.00(1H, dd, J=3.8, 5.1 Hz), 6.46(1H, d, J=15.4 Hz), 5.72 (2H, brs), 4.00–3.70(4H, m), 2.00–1.45(4H, m), 1.10–0.80 (6H, m)

Substantially the same procedure as in Example 5 was repeated using 7.29 g (20.1 mmol) of Compound j to give 5.54 g (yield: 80%) of Compound 17 as pale yellow crystals.

Melting point: 269.6° to 270.5° C. (recrystallized from dioxane-water)

Elemental analysis: $C_{17}H_{20}N_4O_4S$ Calcd.(%): C, 59.28; H, 5.85; N, 16.26 Found (%): C, 59.31; H, 5.77; N, 16.37

IR (KBr), $v_{max}$(cm$^{-1}$): 1704, 1651, 1592

NMR DMSO-d$_6$, δ (ppm): 13.44(1H, brs), 7.78(1H, d, J=16.0 Hz), 7.60(1H, d, J=5.0 Hz), 7.40(1H, d, J=3.5 Hz), 7.12(1H, dd, J=3.5, 5.0 Hz), 6.62(1H, d, J=16.0 Hz), 4.00 (2H, t), 3.85(2H, t), 1.8–1.5(4H, m), 0.95–0.80(6H, m)

Example 18

1,3-Dipropyl-7-methyl-8-[2-(E)-(2-thienyl)vinyl] xanthine (Compound 18)

Substantially the same procedure as in Example 2 was repeated using 3.90 g (11.3 mmol) of Compound 17 obtained in Example 17 to give 3.84 g (yield: 95%) of Compound 18 as a pale yellow powder.

Melting point: 184.8° to 185.5° C. (recrystallized from ethanol)

Elemental analysis: $C_{18}H_{22}N_4O_2S$ Calcd.(%): C, 60.31; H, 6.18; N, 15.62 Found (%): C, 60.23; H, 6.09; N, 15.53

IR (KBr), $v_{max}$(cm$^{-1}$): 1688, 1660, 1439, 1417

NMR DMSO-d$_6$, δ (ppm): 7.79(1H, d, J=15.6 Hz), 7.63(1H, d, J=5.0 Hz), 7.52(1H, d, J=3.3 Hz), 7.13(1H, dd, J=3.5–5.0 Hz), 6.96(1H, d, J=15.6 Hz), 4.00(3H, s), 4.00–3.95(2H, m), 3.90–3.80(2H, t), 1.80–1.50(4H, m), 0.95–0.85(6H, m)

Example 19

3-Propyl-8-(E)-styrylxanthine (Compound 19)

Substantially the same procedure as in Example 1 was repeated except that 10.1 g (54.4 mmol) of 5,6-diamino-3-propyluracil (Japanese Published Unexamined Patent Application No. 57517/80) was used in place of 5,6-diamino-1,3-dipropyluracil to give 5.74 g (yield: 35%) of Compound 19 as a white powder.

Melting point: >295° C. (recrystallized from N,N'-dimethylformamide/water)

Elemental analysis: $C_{16}H_{16}N_4O_2$ Calcd.(%): C, 64.85; H, 5.44; N, 18.90 Found (%): C, 65.02; H, 5.37; N, 19.16

IR (KBr), $v_{max}$(cm$^{-1}$): 1689, 1655

NMR DMSO-d$_6$, 90 MHz), δ (ppm): 13.45(1H, brs), 11.03(1H, brs), 7.80–7.20(6H, m), 7.02(1H, d, J=15.9 Hz), 3.92(2H, t), 2.00–1.50(2H, m), 0.93(3H, t)

Example 20

1,3-Dipropyl-8-[2-(E)-(3-pyridyl)vinyl]xanthine (Compound 20)

Substantially the same procedure as in Example 5 was repeated using 5.00 g (22.1 mmol) of 5,6-diamino-1,3-dipropyluracil and 3.63 g (24.3 mmol) of (E)-3-(3-pyridyl) acrylic acid to give 6.56 g (yield: 83%) of a crude product of 6-amino-1,3-dipropyl-5-[3-(E)-(3-pyridyl)acryloyl] aminouracil (Compound k) as a yellow powder.

NMR DMSO-d$_6$, 90 MHz), δ (ppm): 8.95–8.50(3H, m), 8.05(1H, d, J=7.5 Hz), 7.70–7.50(1H, m), 7.57(1H, d, J=17 Hz), 6.95(1H, d, J=17 Hz), 6.70(2H, brs), 3.95–3.65(4H, m), 1.80–1.30(4H, m), 1.00–0.70(6H, m)

Substantially the same procedure as in Example 5 was repeated using 7.65 g (21.4 mmol) of Compound k to give 5.31 g (overall yield: 73%) of Compound 20 as pale yellow needles.

Melting point: 264.8° to 266.7° C. (recrystallized from ethanol)

Elemental analysis: $C_{18}H_{21}N_5O_2$ Calcd.(%): C, 63.70; H, 6.23; N, 20.63 Found (%): C, 63.80; H, 6.35; N, 20.58

IR (KBr), $v_{max}$(cm$^{-1}$): 1708, 1656, 1591, 1575

NMR DMSO-d$_6$, 90 MHz), δ (ppm): 8.80(1H, brs), 8.56(1H, d, J=6.5 Hz), 8.05(1H, d, J=7.5 Hz), 7.63(1H, d, J=16.5 Hz), 7.40(1H, dd, J=6.5, 7.5 Hz), 7.12(1H, d, J=16.5 Hz), 4.15–3.70(4H, m), 2.00–1.40(4H, m), 1.10–0.80(6H, m)

Example 21

1,3-Dipropyl-8-[2-(E)-(4-imidazolyl)vinyl]-7-methylxanthine (Compound 21)

4-Imidazolylacrylic acid (10 g, 72 mmol) was suspended in 100 ml of N,N-dimethylformamide. To the suspension were slowly added 30 ml (216 mmol) of triethylamine and then 40 g (145 mmol) of trityl chloride with stirring under ice cooling. The mixture was stirred at room temperature for 2 hours, and then concentrated under reduced pressure, followed by addition of 300 ml of water. The aqueous solution was extracted three times with chloroform, and the organic layers were combined and washed twice with water and once with a saturated aqueous solution of sodium chloride. After the mixture was dried over anhydrous sodium sulfate, the solvent was distilled off under reduced pressure, and the residue was purified by silica gel column chromatography (eluent: 5% methanol/chloroform) to give 27.5 g of a mixture of (1-trityl-4-imidazolyl)acrylic acid and (3-trityl-4-imidazolyl)acrylic acid as a white powder.

Substantially the same procedure as in Example 5 was repeated using 3.70 g (9.73 mmol) of the obtained carboxylic acid mixture and 2.00 g (8.85 mmol) of 5,6-diamino-1,3-dipropyluracil to give 2.62 g (overall yield: 52%) of a mixture of 1,3-dipropyl-8-[2-(E)-(1-trityl-4-imidazolyl) vinyl]xanthine (Compound 1) and 1,3-dipropyl-8-[2-(E)-(3-trityl-4-imidazolyl)vinyl]xanthine (Compound m) as a white powder.

NMR (CDCl$_3$), δ (ppm): 12.40(1H, brs), 7.64(0.4H, s), 7.62(1H, s), 7.58(0.6H, s), 7.40–6.99(17H, m), 4.10–3.90 (4H, m), 1.85–1.60(4H, m), 1.05–0.85(6H, m)

The same procedure as in Example 2 was repeated using 1.96 g (3.44 mmol) of the mixture of Compound 1 and Compound m to give a crude product. The crude product was dissolved in 50 ml of methanol, and 1.5 ml of 1N hydrochloric acid was added to the solution, followed by stirring at 50° C. for 2 hours. After the solution was concentrated to about a half of its original volume, the concentrate was adjusted to pH 4 and extracted six times with chloroform. The organic layers were combined and dried over anhydrous sodium sulfate, and the solvent was distilled off under reduced pressure. The residue was purified by silica gel column chromatography (eluent: 10% methanol/chloroform) to give 640 mg (overall yield: 55%) of Compound 21 as an amorphous substance. The obtained Compound 21 (2.00 g) was treated with a hydrogen chloride/methanol solution and then recrystallized from isopropanol to give 1.04 g of hydrochloride of Compound 21.

Melting point: 236.8° to 243° C. Elemental analysis: $C_{17}H_{22}N_6O_2 \cdot HCl$ Calcd.(%): C, 53.89; H, 6.11; N, 22.18 Found (%): C, 53.82; H, 6.05; N, 22.16

IR (KBr), $v_{max}(cm^{-1})$: 1699, 1661

NMR DMSO-$d_6$), δ (ppm): 9.17(1H, s), 7.99(1H, s), 7.75(1H, d, J=16.1 Hz), 7.51(1H, d, J=16.1 Hz), 4.01(3H, s), 3.97(2H, t), 3.83(2H, t), 1.80–1.50(4H, m), 0.95–0.80(6H, m)

Example 22

3-Propyl-8-[(E)-3,4,5-trimethoxystyryl]xanthine (Compound 22)

5,6-Diamino-1-propyluracil (2.00 g, 11 mmol) was suspended in 40 ml of N,N-dimethylformamide. To the suspension were added 3.37 g (16 mmol) of N,N'-dicyclohexylcarbodiimide and 2.00 g (13 mmol) of 1-hydroxybenzotriazole. Then, 2.59 g (11 mmol) of 3,4,5-trimethoxycinnamic acid was slowly added thereto in several portions, and the mixture was stirred overnight at room temperature. After insoluble substances were removed by filtration, the filtrate was concentrated under reduced pressure and 40 ml of a 2N aqueous solution of sodium hydroxide was added to the residue. The mixture was heated under reflux for 30 minutes, followed by neutralization. Deposited crystals were collected by filtration and recrystallized from isopropanol/water to give 2.51 g (overall yield: 60%) of Compound 22 as a yellow powder.

Melting point: 286.0° to 290.6° C.

Elemental analysis: $C_{19}H_{22}N_4O_5 \cdot H_2O$ Calcd.(%): C, 56.43; H, 5.98; N, 13.85 Found (%): C, 56.41; H, 6.04; N, 13.59

IR (KBr), $v_{max}(cm^{-1})$: 1685, 1659, 1585, 1508

NMR DMSO-$d_6$, 90 MHz), δ (ppm):
7.60(1H, d, J=16.5 Hz), 7.05(1H, d, J=16.5 Hz), 6.98(2H, s), 4.10–3.85(2H, m), 3.85(6H, s), 3.70(3H, s), 1.90–1.45 (2H, m), 0.91(3H, t)

Example 23

1,3-Diallyl-8-[(E)-3,4,5-trimethoxystyryl]xanthine (Compound 23)

Substantially the same procedure as in Example 5 was repeated using 3.0 g (13.5 mmol) of 1,3-diallyl-5,6-diaminouracil and 3.55 g (14.9 mmol) of 3,4,5-trimethoxycinnamic acid to give 4.48 g (yield: 75%) of 6-amino-1,3-diallyl-5-[(E)-3,4,5-trimethoxycinnamoyl] aminouracil (Compound n) as an amorphous substance.

NMR (CDCl$_3$, 90 MHz), δ (ppm): 7.90(1H, brs), 7.56(1H, d, J=16.0 Hz), 6.71(2H, s), 6.57(1H, d, J=16.0 Hz), 6.15–5.60(4H, m), 5.50–5.05(4H, m), 4.75–4.45(4H, m), 3.90(9H, s)

Substantially the same procedure as in Example 5 was repeated using 4.34 g (9.82 mmol) of Compound n to give 2.81 g (yield: 68%) of Compound 23 as a pale yellowish green powder.

Melting point: 253.1° to 255.4° C. (recrystallized from dioxane)

Elemental analysis: $C_{22}H_{24}N_4O_5 \cdot 1/2 H_2O$ Calcd.(%): C, 60.96; H, 5.81; N, 12.93 Found (%): C, 61.05; H, 5.60; N, 12.91

IR (KBr), $v_{max}(cm^{-1})$: 1704, 1645, 1583, 1510

NMR (CDCl$_3$), δ (ppm): 12.94(1H, brs), 7.73(1H, d, J=16.3 Hz), 7.05(1H, d, J=16.3 Hz), 6.81(2H, s), 6.12–5.92 (2H, m), 5.37–5.22(4H, m), 4.83–4.76(4H, m), 3.91(6H, s), 3.90(3H, s)

Example 24

1,3-Diallyl-7-methyl-8-[(E)-3,4,5-trimethoxystyryl] xanthine (Compound 24)

Substantially the same procedure as in Example 2 was repeated using 1.13 g (2.67 mmol) of Compound 23 obtained in Example 23 to give 620 mg (yield: 53%) of Compound 24 as pale yellow needles.

Melting point: 189.0° to 191.1° C. (recrystallized from ethyl acetate)

Elemental analysis: $C_{23}H_{26}N_4O_5$ Calcd.(%): C, 63.00; H, 5.97; N, 12.77 Found (%): C, 63.00; H, 6.05; N, 12.85

IR (KBr), $v_{max}(cm^{-1})$: 1699, 1660

NMR (CDCl$_3$, 90 MHz), δ (ppm): 7.78(1H, d, J=16.0 Hz), 6.85(2H, s), 6.84(1H, d, J=16.0 Hz), 6.30–5.75(2H, m), 5.45–5.10(4H, m), 4.85–4.55(4H, m), 4.07(3H, s), 3.92(6H, s), 3.90(3H, s)

Example 25

1,3-Dibutyl-8-[(E)-3,4,45-trimethoxystyryl]xanthine (Compound 25)

Substantially the same procedure as in Example 5 was repeated using 4.75 g (18.7 mmol) of 5,6-diamino-1,3-dibutyluracil and 4.90 g (20.6 mmol) of 3,4,5-trimethoxycinnamic acid to give 10.6 g of a crude product of 6-amino-1,3-dibutyl-5-[(E)-3,4,5-trimethoxycinnamoyl] aminouracil (Compound o) as an amorphous substance.

NMR (CDCl$_3$, 90 MHz), δ (ppm): 7.85(1H, brs), 7.53(1H, d, J=16.0 Hz), 6.72(2H, s), 6.57(1H, d, J=16.0 Hz), 5.74(2H, brs), 4.05–3.70(4H, m), 3.89(9H, s), 1.80–1.15(8H, m), 1.15–0.80(6H, m)

Substantially the same procedure as in Example 5 was repeated using 10.6 g of Compound o to give 5.80 g (overall yield: 68%) of Compound 25 as a white powder.

Melting point: 205.8° to 207.2° C. (recrystallized from ethyl acetate)

IR (KBr), $v_{max}(cm^{-1})$: 1698, 1643, 1584, 1570, 1504

Elemental analysis: $C_{24}H_{32}N_4O_5$ Calcd.(%): C, 63.14; H, 7.06; N, 12.27 Found (%): C, 63.48; H, 6.71; N, 12.43

NMR (CDCl$_3$, 90 MHz), δ (ppm): 7.75(1H, d, J=15.8 Hz), 6.98(1H, d, J=15.8 Hz), 6.82(2H, s), 4.30–4.12(4H, m), 3.98(6H, s), 3.93(3H, s), 2.00–0.80(14H, m)

Example 26

1,3-Dibutyl-7-methyl-8-[(E)-3,4,5-trimethoxystyryl] xanthine (Compound 26)

Substantially the same procedure as in Example 2 was repeated using 2.50 g (5.48 mmol) of Compound 25 obtained in Example 25 to give 2.36 g (yield: 92%) of Compound 26 as a pale green powder.

Melting point: 136.8° to 137.3° C. (recrystallized from ethanol/water)

Elemental analysis: $C_{25}H_{34}N_4O_5$ Calcd.(%): C, 63.81; H, 7.28; N, 11.91 Found (%): C, 63.63; H, 6.93; N, 11.99

IR (KBr), $v_{max}(cm^{-1})$: 1692, 1659

NMR (CDCl$_3$, 90 MHz), δ (ppm): 7.68(1H, d, J=15.8 Hz), 6.80(2H, s), 6.79(1H, d, J=15.8 Hz), 4.30–3.90(4H, m), 4.03(3H, s), 3.95(6H, s), 3.91(3H, s), 1.90–1.10(8H, m), 1.05–0.80(6H, m)

Preparation Example 1

Tablets

Tablets each having the following composition are prepared in a conventional manner.

| | |
|---|---|
| Compound 2 | 20 mg |
| Lactose | 60 mg |
| Potato starch | 30 mg |
| Polyvinyl alcohol | 3 mg |
| Magnesium stearate | 1 mg |

Preparation Example 2

Powder preparation

A powder preparation having the following composition is prepared in a conventional manner.

| | |
|---|---|
| Compound 10 | 20 mg |
| Lactose | 300 mg |

Preparation Example 3

Syrup preparation

A syrup preparation having the following composition is prepared in a conventional manner.

| | |
|---|---|
| Compound 11 | 20 mg |
| Refined sugar | 30 mg |
| Ethyl p-hydroxybenzoate | 40 mg |
| Propyl p-hydroxybenzoate | 10 mg |
| Strawberry flavor | 0.1 cc |

A mixture of the above ingredients is made up to 100 cc with water.

Preparation Example 4

Capsules

Capsules each having the following composition are prepared in a conventional manner.

| | |
|---|---|
| Compound 2 | 20 mg |
| Lactose | 200 mg |
| Magnesium stearate | 5 mg |

A mixture of the above ingredients is loaded into gelatin capsules.

We claim:

1. A xanthine derivative of the formula:

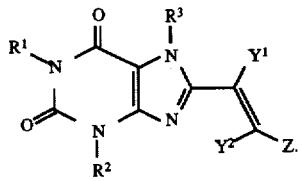

wherein $R^1$ and $R^2$ are the same or different and each represents a propyl group, a butyl group or an allyl group; $R^3$ represents a hydrogen atom or a lower alkyl group; $Y^1$ and $Y^2$ are the same or different and each represents a hydrogen atom or a methyl group; and Z represents a substituted or unsubstituted phenyl group wherein the substituents are lower alkyl, hydroxy, lower alkoxy, halogen, amino or nitro, a pyridyl group, an imidazolyl group, a furyl group or a thienyl group, or a pharmaceutically acceptable salt thereof.

* * * * *

UNITED STATES PATENT AND TRADEMARK OFFICE
CERTIFICATE OF CORRECTION

PATENT NO. : 5,756,735

DATED : May 26, 1998

INVENTOR(S): FUMIO SUZUKI ET AL.

It is certified that error appears in the above-identified patent and that said Letters Patent is hereby corrected as shown below:

COLUMN 3

Line 5-11 " 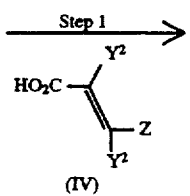 " should read -- 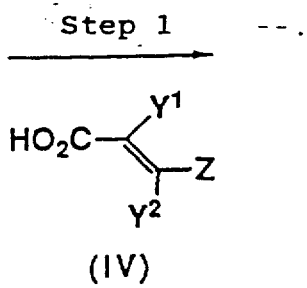 --.

COLUMN 9

Line 30, "A1" should read --$A_1$--.

COLUMN 12

Line 23, "[$10^4$M" should read --[$10^{-4}$M--.

COLUMN 13

Line 30, "width 4533 height" should read
--width 45 X height--.

UNITED STATES PATENT AND TRADEMARK OFFICE
CERTIFICATE OF CORRECTION

PATENT NO. : 5,756,735

DATED : May 26, 1998

INVENTOR(S) : FUMIO SUZUKI ET AL.

It is certified that error appears in the above-identified patent and that said Letters Patent is hereby corrected as shown below:

COLUMN 15

Line 25, "$C_{19}H_{22}N_4O_2$ calcd.(%):C," should read
--$C_{19}H_{22}N_4O_2$ ¶ Calcd.(%):C,--.
Line 26, "16.56 Found (%):" should read
--16.56 ¶ Found (%)--.
Line 28, "1.3.59(1M," should read --13.59(1M,--.

COLUMN 17

Line 29, "(DMSO-d6)," should read --(DMSO-$d_6$),--.
Line 53, "$C_{19}H_{20}C_{12}N_4O_2$" should read
--$C_{19}H_{20}Cl_2N_4O_2$--.
Line 56, "DMSO-$d_6$)," should read --(DMSO-$d_6$),--.

COLUMN 18

Line 8, "DMSO-$d_6$)," should read --(DMSO-$d_6$),--.
Line 36, "$V_{max}$(cm$^-$):" should read --$V_{max}$(cm$^{-1}$):--.
Line 55, "DMSO-$d_6$)," should read --(DMSO-$d_6$),--.

COLUMN 19

Line 17, "DMSO-$d_6$)," should read --(DMSO-$d_6$),--.
Line 37, "DMSO-$d_6$)," should read --(DMSO-$d_6$),--.

UNITED STATES PATENT AND TRADEMARK OFFICE
CERTIFICATE OF CORRECTION

PATENT NO. : 5,756,735

DATED : May 26, 1998

INVENTOR(S) : FUMIO SUZUKI ET AL.

It is certified that error appears in the above-identified patent and that said Letters Patent is hereby corrected as shown below:

COLUMN 20

Line 33, "DMSO-$d_6$-$D_2$O," should read --(DMSO-$d_6$-$D_2$O,--.
Line 47, "DMSO-$d_6$)," should read --(DMSO-$d_6$),--.

COLUMN 21

Line 28, "DMSO-$d_6$)," should read --(DMSO-$d_6$),--.
Line 48, "DMSO-$d_6$)," should read --(DMSO-$d_6$),--.

COLUMN 22

Line 1, "DMSO-$d_6$," should read --(DMSO-$d_6$,--.
Line 15, "DMSO-$d_6$," should read --(DMSO-$d_6$,--.
Line 28, "DMSO-$d_6$," should read --(DMSO-$d_6$,--.

COLUMN 23

Line 16, "C.Elemental" should read
   --C. ¶ Elemental--.
Line 20, "DMSO-$d_6$)," should read --(DMSO-$d_6$),--.
Line 49, "DMSO-$d_6$," should read --(DMSO-$d_6$,--.

UNITED STATES PATENT AND TRADEMARK OFFICE
CERTIFICATE OF CORRECTION

PATENT NO. : 5,756,735

DATED : May 26, 1998

INVENTOR(S) : FUMIO SUZUKI ET AL.

It is certified that error appears in the above-identified patent and that said Letters Patent is hereby corrected as shown below:

COLUMN 24

Line 7, "$C_{22}H_{24}N_4O_51/2H_2O$" should read --$C_{22}H_{24}N_4O_5 \cdot 1/2H_2O$--.

Signed and Sealed this

Twenty-fifth Day of July, 2000

Attest:

Attesting Officer

Q. TODD DICKINSON

Director of Patents and Trademarks